United States Patent
Hahn et al.

(10) Patent No.: US 8,672,950 B2
(45) Date of Patent: Mar. 18, 2014

(54) UTERUS-MANIPULATOR

(75) Inventors: Martin Hahn, Altheim (DE); Frank Doll, Talheim (DE); Anne-Kathrin Graf, Muehlheim-Stetten (DE); Sven Steckeler, Rottenburg (DE)

(73) Assignee: Karl Storz GmbH & Co. KG (DE)

( * ) Notice: Subject to any disclaimer, the term of this patent is extended or adjusted under 35 U.S.C. 154(b) by 60 days.

(21) Appl. No.: 12/902,823

(22) Filed: Oct. 12, 2010

(65) Prior Publication Data

US 2011/0092982 A1 Apr. 21, 2011

(30) Foreign Application Priority Data

Oct. 12, 2009 (DE) .................. 10 2009 049 169

(51) Int. Cl.
*A61B 17/42* (2006.01)
(52) U.S. Cl.
USPC ........................................ 606/119
(58) Field of Classification Search
USPC .......... 606/119, 193; 600/184, 201, 204, 206, 600/207, 208; 604/101.01, 105.01; 128/831, 832, 833
See application file for complete search history.

(56) References Cited

U.S. PATENT DOCUMENTS

| | | | |
|---|---|---|---|
| 5,104,377 A | 4/1992 | Levine | |
| 5,431,662 A * | 7/1995 | Nicholas | 606/119 |
| 5,643,311 A | 7/1997 | Smith et al. | |
| 5,716,329 A * | 2/1998 | Dieter | 600/210 |
| 2006/0173486 A1 * | 8/2006 | Burke et al. | 606/193 |
| 2007/0010782 A1 * | 1/2007 | Doty et al. | 604/20 |
| 2007/0055132 A1 | 3/2007 | Camus et al. | |
| 2008/0109010 A1 | 5/2008 | Feuer et al. | |

FOREIGN PATENT DOCUMENTS

DE 102005042338 A1 3/2007

OTHER PUBLICATIONS

The Free Dictionary definition of "retroversion" as accessed on Jan. 29, 2013; http://medical-dictionary.thefreedictionary.com/retroversion.*
The Free Dictionary definition of "anteversion" as accessed on Jan. 29, 2013; http://medical-dictionary.thefreedictionary.com/anteversion.*

* cited by examiner

*Primary Examiner* — Ryan Severson
*Assistant Examiner* — Jonathan W Miles
(74) *Attorney, Agent, or Firm* — St. Onge Steward Johnston & Reens LLC

(57) ABSTRACT

A micro-invasive medical instrument includes a shaft and an end balloon on a distal end of the shaft, where the end balloon completely encloses the distal end of the shaft.

10 Claims, 1 Drawing Sheet

UTERUS-MANIPULATOR

CROSS-REFERENCE TO RELATED APPLICATIONS

The present application claims priority of German patent application No. 10 2009 049 169.4 filed on Oct. 12, 2009.

FIELD OF THE INVENTION

The present invention relates to a micro-invasive medical instrument, in particular a uterus manipulator.

BACKGROUND OF THE INVENTION

U.S. Pat. No. 5,104,377 describes a device to insert fluids or other instruments into the uterus. The device includes two balloons for positioning inside or outside the cervix uteri.

In U.S. Pat. No. 5,643,311 a uterus manipulator is described whose distal section can be moved by means of a joint or articulated linkage. The distal end comprises a soft silicon tip.

Conventional uterine manipulators and other devices for insertion into the uterus or other body cavities comprise thin ends that, even when made of silicon or another soft material, make possible a pointed impact on the sensitive mucous membrane of the uterus or other organs and thus constitute a risk of injury.

It is an object of the present invention to provide an improved micro-invasive medical instrument, in particular an improved uterus manipulator, and an improved distal segment for such a micro-invasive medical instrument.

SUMMARY OF THE INVENTION

The foregoing and other objects are achieved by the embodiments of the invention described herein.

Various embodiments of the present invention are based on the idea of providing, on a distal end of a shaft of a micro-invasive medical instrument or of a distal segment for a micro-invasive medical instrument, an end balloon that completely encloses the distal end of the instrument or of the distal segment for the instrument. The end balloon encloses the distal end of the shaft completely, in that it not only surrounds the shaft azimuthally on the longitudinal axis of the shaft, but also forms the entire distal end face of the instrument. The end balloon in every case comprises on its proximal end an aperture in which the shaft of the instrument is positioned, so that the distal end of the shaft is positioned inside the end balloon and proximal segments of the shaft are positioned outside the end balloon.

The end balloon is inflatable or can be expanded by introducing a fluid and is therefore especially atraumatic. Even when the end balloon is in inflated or expanded state, or is filled with a fluid, and touches an organ from the inside or outside and exerts a force on said organ, this force, owing to the extensive and elastic skin or wall of the balloon, is distributed over such a great surface that only a minimum pressure occurs. Because of the suppleness of the balloon or of its wall, local pressure points are effectively avoided. Consequently the risk of injury is considerably lessened, especially when for example, as in the case of a uterus manipulator, a force is meant to be, and must be, exerted in order to move an organ.

A micro-invasive medical instrument, in particular a uterus manipulator, includes a shaft and an inflatable end balloon on a distal end of the shaft, and the inflatable end balloon completely encloses the distal end of the instrument. The instrument can also comprise a supporting balloon on the shaft, which is at a distance from the distal end of the shaft. In the case of a uterus manipulator, the supporting balloon is configured in particular to be positioned in the cervix (cervix uteri) or on or at the internal os of the uterus (ostium uteri internum). Between the end balloon and the supporting balloon a lateral aperture can be provided on the shaft, through which a fluid (such as for pertubation) or an object (for example an endoscopic instrument) can be pushed out of the shaft toward the outside.

A first channel, whose lumen at the distal end is connected with the inside of the end balloon, and a second channel, whose lumen at the distal end is connected with the inside of the supporting balloon, can be provided in or on the shaft. Through these two channels the end balloon and the supporting balloon can be inflated or expanded independently of one another or their sizes can be adjusted. Alternatively, a single channel can be provided that is connected with the interior spaces both of the end balloon and of the supporting balloon, in order to be able to fill both balloons with a fluid.

Alternatively to inflatability, the end balloon can be spread open, expanded, unfolded or enlarged by means of one or more braces or other tractive elements and/or other mechanical devices. The same can apply in some cases for the supporting balloon. In certain cases both balloons can be inflatably expanded, spread open, unfolded or enlarged, both balloons by means of one or more braces or other tractive elements and/or other mechanical devices or one of the two balloons in one way and one in the other way.

For example, the end balloon and/or in some cases the supporting balloon comprises a membrane of an elastic material, which assumes an expanded form when it is in loosened or non-tensed or low-tension state. One or more braces or other tractive elements are secured to the membrane in such a way that the volume and cross-section of the particular balloon can be reduced by traction on the brace or braces or other tractive elements. For this purpose the brace or braces or other tractive elements are secured, for example on the inside of the membrane or at one or more sites. These sites are located, for example, as far as possible from a longitudinal axis of the instrument when the membrane is in expanded form, so that the brace or braces or other tractive elements are positioned to exert a traction inward in the radial direction. Alternatively the brace or braces or other tractive elements, for example, are secured and positioned and aligned on a proximal end or edge of the balloon or membrane in order to exert a traction in the longitudinal direction of the instrument toward the proximal end.

Alternatively, the end balloon and/or in certain cases the supporting balloon comprises a membrane made of an elastic material, which in the loosened or non-tensed or low-tension state has a small volume and a small cross-section. The brace or braces or other tractive elements are arranged and secured to the membrane in such a way that the membrane when pulled in the longitudinal direction of the instrument becomes compressed, while the membrane is configured in such a way that it expands radially at the same time. For this purpose the brace or braces or other tractive elements, for example, are secured and positioned on a proximal end or border of the balloon in order to exert a pull in the distal direction. A similar effect can be achieved with a thrusting element, which engages at the same site and is positioned and configured to exert a thrust in the distal direction.

The instrument can comprise a joint between a proximal segment and a distal segment of the shaft, so that the end balloon and in certain cases the supporting balloon are positioned on the distal segment of the shaft. Thus, for example, after inserting the distal segment in the cervix and uterus, the uterus can be moved. This is often necessary or at least advantageous, among other cases, in laparoscopic procedures in the pelvic region and in the lower abdominal region. A force exerted by the uterus manipulator on the uterus is distributed over a wide area by the end balloon, which completely encloses the distal end of the shaft. This minimizes the risk of injury.

To reduce further the risk of injury, in particular upon inserting the instrument, all radii of curvature on the distal end of the shaft enclosed by the end balloon are equal to at least a fourth, or still better at least a third, of the diameter of the shaft or of the maximum measurement of the cross-section of the shaft. A hemispheric-shaped end of the shaft is particularly advantageous, where the radii of curvature correspond to the diameter of the shaft, which is in particular cylindrical in shape.

Between a proximal segment of the shaft and a distal segment of the shaft, a coupling can be configured for repeated releasable mechanical and functional coupling of the two segments. Here in particular the proximal segment is intended and configured for repeated use (that is, in particular, autoclavable), while the distal segment is provided and configured for a single application or for one-time use. On configuring the distal segment for one-time use, the segment is manufactured in cost-effective manner, is not autoclavable or at least not repeatedly, because of its materials and surfaces, and is less robust than when configured for repeated use.

A distal segment for a micro-invasive medical instrument, in particular for a uterus manipulator, includes a shaft segment, a coupling to couple the distal segment with a proximal shaft segment, and an inflatable end balloon on a distal end of the shaft segment, where the inflatable end balloon completely encloses the distal end of the shaft segment. The distal segment can, in addition, comprise a supporting balloon on the shaft segment, which is at a distance from the distal end of the shaft segment.

In addition, the distal segment can comprise a lateral aperture on the shaft segment between the end balloon and the supporting balloon, through which a fluid (for example for pertubation) or an object (for example an endoscopic instrument) can be pushed out of the shaft segment to the outside. A first channel, whose lumen on the distal end is connected with the inside of the end balloon, and a second channel, whose lumen on the distal end is connected with the inside of the supporting balloon, can be included in or on the shaft segment.

All radii of curvature on the distal end of the shaft segment are equal to at least one-fourth or at least one-third of the diameter of the shaft segment. The distal segment, in particular, is configured for one-time application or one-time use and then for disposal.

BRIEF DESCRIPTION OF THE DRAWINGS

Hereinafter, embodiments are described in greater detail with reference to the appended drawings.

DETAILED DESCRIPTION OF THE INVENTION

Figure 1:
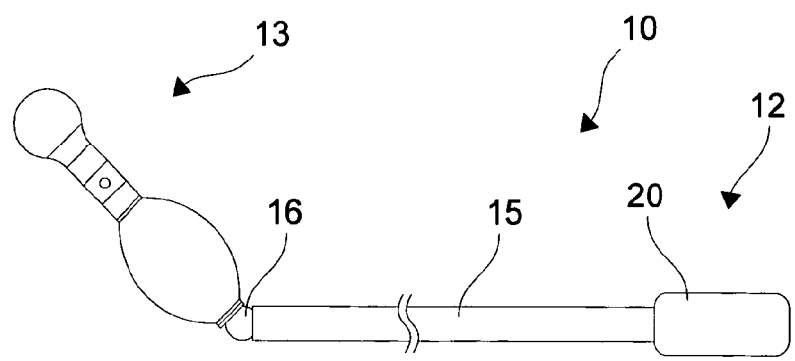
FIG. 1 shows a schematic depiction of a micro-invasive medical instrument, in particular a uterus manipulator.

FIG. 1 shows a schematic depiction of a uterus manipulator 10 as an example of a micro-invasive medical instrument. The uterus manipulator 10 includes a proximal segment 12 and a distal segment 13 for insertion into the cervix and uterus. The uterus manipulator 10 includes a shaft 15, which extends from the proximal segment 12 to the distal segment 13. A joint 16 is positioned between a proximal segment and a distal segment of the shaft 15.

On the proximal end the shaft 15 is connected with a gripping device 20, which is shown only schematically in FIG. 1. The gripping device is configured for handling, guiding, and control of the uterus manipulator 10 and can include properties that clearly diverge from the schematic depiction in FIG. 1. The distal segment 13 of the uterus manipulator 10 is described in greater detail hereinafter with reference to FIGS. 2 and 3. The optional joint 16 is configured for an anteversion and/or retroversion of the uterus by an angle that can be controlled by the gripping device 20.

Figure 2:
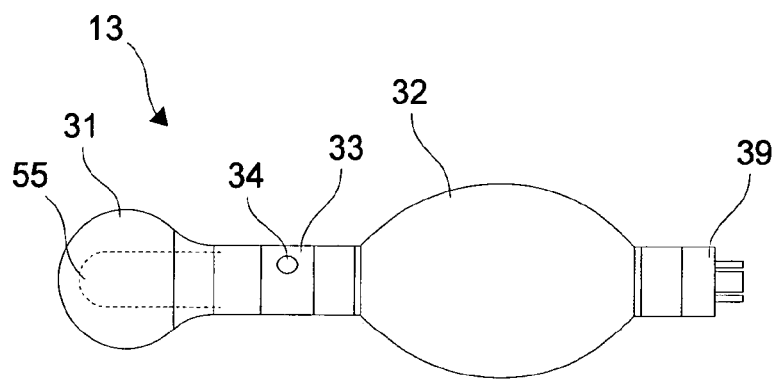
FIG. 2 shows a schematic depiction of a distal segment for a micro-invasive medical instrument.
Figure 3:
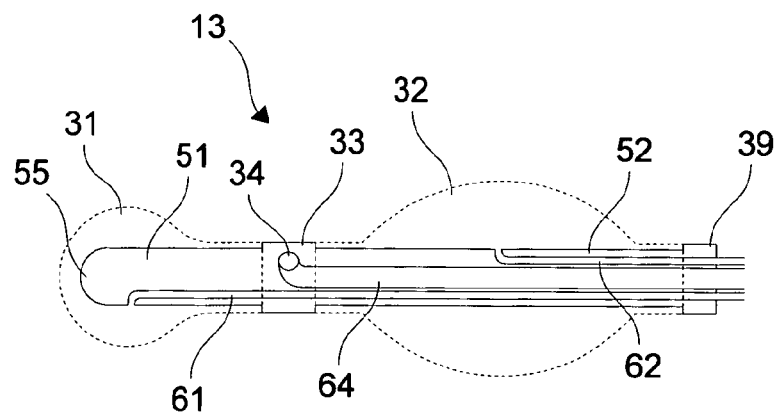
FIG. 3 shows an additional schematic depiction of the distal segment from FIG. 2.

FIGS. 2 and 3 show schematic views of a distal segment 13 of a uterus manipulator, as presented above, for example with reference to FIG. 1. FIG. 2 presents a lateral view of the uterus manipulator, so that the longitudinal axis of the uterus manipulator or the longitudinal axis of its segments is parallel to the plane of projection. Contrary to FIG. 2, FIG. 3 partially shows a cross-section.

The distal segment 13 includes an end balloon 31 and a supporting balloon 32, which are positioned at a distance from one another and each of which is shown in expanded state. Contrary to the depiction in FIGS. 2 and 3, the end balloon 31 and the supporting balloon 32 can border immediately on one another or can comprise a common inner area with a thin portion between the end balloon 31 and the supporting balloon 32. The end balloon 31 and supporting balloon 32 each comprise a wall or skin of silicon, rubber, another elastomer or another elastic material that is in particular biocompatible. The end balloon 31 completely encloses a distal end 55 of a shaft segment that is described hereinafter in more detail with reference to FIG. 3.

A particularly straight shaft segment 33 with an especially circular or elliptical cross-section and an aperture 34 is positioned in the end balloon 31, in the supporting balloon 32, and between the end balloon 31 and the supporting balloon 32. A fluid for pertubation or an endoscopic instrument, for example, can be pushed outward from the shaft segment 33 through the aperture 34.

In addition, the distal segment 13 includes a coupling 39 for mechanical (for example by form-locking or force-fitting) and functional coupling of the distal segment 13 with a proximal segment of a uterus manipulator or other micro-invasive medical instrument. The distal segment 13 presented here with reference to FIGS. 2 and 3 is distinguished from the one presented above with reference to FIG. 1 by the coupling 39, which can be provided instead of the joint 16 or in addition to it. A joint can, for example, contrary to FIGS. 2 and 3, be positioned between the coupling 39 and the supporting balloon 32. Alternatively a joint can be positioned, for example proximally from the coupling 39, in a proximal segment of the uterus manipulator.

The end balloon 31 and the supporting balloon 32 are illustrated with broken lines and as two separate components. The elastic components, which connect the end balloon 31 and the supporting balloon 32, are connected, for example by form-locking, force-fitting or firm bonding, with the shaft segment 33. A form-locking connection includes for example, one or more studs on the end balloon 31 or in the supporting balloon 32, which engage in corresponding grooves on the shaft segment 33. A force-fitting connection is produced, for example, by an elastic resetting force of the component that constitutes the end balloon 31 or the supporting balloon 32 and by static friction between the latter and the shaft segment 33. Contrary to FIG. 3, the end balloon 31 and the supporting balloon 32 can be configured from a single joint component in which the aperture 34 is then also positioned.

One area 51 of the shaft segment 33 is positioned in the end balloon 31. The area 51 of the shaft segment 33 includes the distal end of the shaft segment 33, which is completely enclosed by the end balloon 31. An area 52 of the shaft segment 33 is positioned in the supporting balloon 32 or is surrounded by it.

A first channel 61, a second channel 62 and a third channel 64 are positioned in the shaft segment 33. On the proximal end the three channels 61, 62, 64 end at the coupling 39. The coupling 39 is configured in order to connect the lumina of the channels 61, 62, 64 with corresponding lumina of the corresponding channels of the proximal segment, upon coupling of the distal segment 13 with a proximal segment of a micro-invasive medical instrument.

The first channel 61 is connected with the inside or the hollow area of the end balloon 31 by an aperture on its distal end in the area 51 of the shaft segment 33. The second channel 62 is connected with the inside or the hollow area of the supporting balloon 32 by an aperture on its distal end in the area 52 of the shaft segment 33. The third channel 64 is connected with the aperture 34. The first channel 61 and the second channel 62 are configured to convey fluids to the end balloon 31 or to the supporting balloon 32 or away from the end balloon 31 and supporting balloon 32. Instead of two separate channels 61, 62, a common channel can be provided which is connected with the inside of the end balloon 31 and of the supporting balloon 32. The third channel 64 is configured to conduct a fluid or to guide an instrument to the aperture 34.

The distal end 55 of the area 51 of the shaft segment 33 is shown in FIG. 3 with a hemispheric shape. Here, at every site, the surface of the distal end 55 has a radius of curvature that corresponds to half of the diameter of the area 51 of the shaft segment 33. Contrary to this, the distal end 55 can take other forms. To minimize the risk of injury, the distal end 55 preferably has a shape in which, at least on all distally oriented surface areas, the radius of curvature is at least a fourth or at least a third of the diameter of the area 51 of the shaft segment 33. In the event of a non-circular cross-section of the area 51 of the shaft segment 33, the radius of curvature on the distal end 55 is at least a fourth or at least a third of the maximum linear dimension of the cross-section of the area 51 of the shaft segment 33.

What is claimed is:

1. A micro-invasive medical instrument, comprising:
a shaft with a distal segment;
an end balloon on a distal end of the shaft;
a supporting balloon on the shaft, which is at a distance from the distal end of the shaft;
a proximal segment of the shaft;
a coupling releasably coupling the distal segment with the proximal segment; and
a joint positioned between the proximal segment and the distal segment of the shaft, said joint is articulable to provide anteversion and retroversion;
wherein the end balloon completely encloses the distal end of the shaft; and
wherein the end balloon and the supporting balloon are positioned on the distal segment of the shaft.

2. The instrument according to claim 1, further comprising:
a lateral aperture on the shaft between the end balloon and the supporting balloon, through which a liquid is conducted or an object can be pushed out of the shaft to the outside of the shaft.

3. The instrument according to claim 1, further comprising:
a first channel in or on the shaft, whose lumen on the distal end is connected with the inside of the end balloon; and
a second channel in or on the shaft, whose lumen on the distal end is connected with the inside of the supporting balloon.

4. The instrument according to claim 1, wherein the radius of curvature on the distal end of the shaft is equal to at least a fourth of the diameter of the shaft.

5. The instrument according to claim 1, wherein the instrument is a uterus manipulator.

6. A distal segment for a micro-invasive medical instrument, comprising:
a shaft segment;
an end balloon on a distal end of the shaft segment;
a supporting balloon on the shaft segment, which is at a distance from the distal end of the shaft segment;
a coupling releasably coupling the distal segment with a proximal shaft segment; and
a joint positioned between the proximal shaft segment and the distal segment, said joint is articulable to provide anteversion and retroversion;
the end balloon and the supporting balloon are positioned distal to the joint;
wherein the end balloon completely encloses the distal end of the shaft segment.

7. The distal segment according to claim 6, further comprising:
a lateral aperture on the shaft segment between the end balloon and the supporting balloon, through which a fluid can be conducted or an object can be pushed out of the shaft segment to the outside of the shaft.

8. The distal segment according to claim 7, further comprising:
a first channel in or on the shaft segment, whose lumen is connected on the distal end with the inside of the end balloon; and
a second channel in or on the shaft segment, whose lumen is connected on the distal end with the inside of the supporting balloon.

9. The distal segment according to claim 6, wherein all radii of curvature on the distal end of the shaft segment are equal to at least a fourth of the diameter of the shaft segment.

10. The distal segment according to claim 6, wherein the distal segment is configured for one-time use and subsequent disposal.

* * * * *